United States Patent [19]

Kumar

[11] Patent Number: 4,657,866
[45] Date of Patent: Apr. 14, 1987

[54] SERUM-FREE, SYNTHETIC, COMPLETELY CHEMICALLY DEFINED TISSUE CULTURE MEDIA

[76] Inventor: Sudhir Kumar, 18901 Springfield, Flossmoor, Ill. 60422

[21] Appl. No.: 769,708

[22] Filed: Sep. 13, 1984

Related U.S. Application Data

[63] Continuation-in-part of Ser. No. 438,159, Dec. 21, 1982, abandoned.

[51] Int. Cl.[4] ............... C12N 5/00; C12N 5/02; C12R 1/91
[52] U.S. Cl. .................... 435/240; 435/241; 435/948
[58] Field of Search .............. 435/240, 241, 948

[56] References Cited
PUBLICATIONS

Honegger et al., "Growth and Differentiation of Aggregating Fetal Brain Cells in a Serum-Free Defined Medium" Nature 282 pp. 305–308 (1979).

Monte, "Hormone-Dependant Growth and Differentiation of Brain Cultured in Serum-Free Medium" Federation Proceedings 38(3) p. 1396 (1979) Abst. #6163.

Del'Aquila et al., "Growth of Normal Human Amnion Epithelial Cells in Serum-Free Medium" Experimental Cellular Research 137 pp. 441–446 (1982).

*Primary Examiner*—Thomas G. Wiseman
*Assistant Examiner*—John E. Tarcza

[57] ABSTRACT

A serum-free, synthetic tissue culture media is described which is completely defined chemically. The two media described can be used for growing all types of human or animal cell lines in tissue culture without addition of any protein, amino acids, hormones, sources of energy, salts, vitamins, etc. with normally used procedures and methods. The media do not require any supplementation with fetal calf serum to support growth of neural cells.

11 Claims, No Drawings

SERUM-FREE, SYNTHETIC, COMPLETELY CHEMICALLY DEFINED TISSUE CULTURE MEDIA

This application is a continuation-in-part of Ser. No. 438,159 filed Dec. 21, 1982, and now abandoned.

SUMMARY OF THE INVENTION

The applicant has developed a serum-free, synthetic tissue culture media which is completely chemically defined. The media can be used to grow all types of animal and human cell lines (e.g. amniotic fluid cells, brain and other tissue cells, lung fibroblasts, white blood cells, etc.) in tissue culture without addition of an outside source of protein (fetal calf serum), hormones or other metabolites. The compositions of culture media solutions (KUMAR MEDIA I and II), which fulfill all requirements of proteins, hormones, salts, vitamins and other metabolites to sustain optimal growth of human and animal cell lines in tissue culture, are being patented by the applicant.

Patent is being solicited on the compositions of the culture media and their use for growing various cells lines in tissue culture. Protection is also being requested from the use of the formula discovered, by making changes/additions/deletions or combinations therof, in the overall compositions/quantities etc. of various components which constitute the culture media.

DESCRIPTION OF DISCOVERY

The petitioner has discovered and formulated the composition of a serum-free, synthetic, completely chemically defined, tissue culture media which does not require any supplementation with fetal calf serum or any other source of protein, hormones, vitamins, or other metabolites. The mixtures, as developed, as complete, fulfill all requirements of protein, amino acids, hormones, vitamins, minerals, salts and other metabolites to sustain optimal growth of human and animal cell lines in tissue culture in vitro, and can be used without any modifications for growing various cell lines (human and animal) in tissue culture. The compositions of the culture media, called by the petitioner, KUMAR MEDIA I and II, are described in Tables 1 and 2, respectively.

The mixtures are prepared by first weighing appropriate quantities of each component, mixing them in large containers and dissolving the contents in deionized, distilled water. The pH of the resultant solutions is adjusted to pH 7.4 with sodium bicarbonate. The solutions are then filtered through a MILLIPORE filter (0.22 u), bottled and sterilized.

The procedures used to grow various animal and human tissue cells in tissue culture using the two media solutions, are the commonly used and accepted methods for growing cells in tissue culture.

TABLE 1

COMPOSITION OF SERUM-FREE, SYNTHETIC, COMPLETELY CHEMICALLY DEFINED TISSUE CULTURE MEDIA - KUMAR MEDIA I

| Item | mg/liter |
| --- | --- |
| Alanine | 60 |
| Alpha-Amino-n-butyric Acid | 5 |
| Arginine | 150 |
| Asparagine | 5 |
| Aspartic Acid | 75 |
| Cysteine-HCl | 100 |

TABLE 1-continued

COMPOSITION OF SERUM-FREE, SYNTHETIC, COMPLETELY CHEMICALLY DEFINED TISSUE CULTURE MEDIA - KUMAR MEDIA I

| Item | mg/liter |
| --- | --- |
| Cystine | 25 |
| Ergothionine | 10 |
| Glutamic Acid | 500 |
| Glutamine | 800 |
| Glycine | 500 |
| Histidine, HCl | 50 |
| Homocysteine | 20 |
| Isoleucine | 75 |
| Leucine | 300 |
| Lysine HCl | 300 |
| Methionine | 50 |
| Ornithine, HCl | 10 |
| Phenylalanine | 100 |
| Proline | 100 |
| Serine | 75 |
| Taurine | 50 |
| Threonine | 100 |
| Tryptophane | 50 |
| Tyrosine | 100 |
| Valine | 200 |
| DL-Alpha-Tocopherol | 2.5 |
| Ascorbic Acid | 25 |
| Biotin | 20 |
| Calciferol | 2.5 |
| Ca—pentothenate | 25 |
| Choline Chloride | 25 |
| Cocarboxylase | 20 |
| Folic Acid | 20 |
| i-Inositol | 15 |
| Menadione | 2.5 |
| Niacin | 5.0 |
| Niacinamide | 20 |
| p-Amniobenzoic Acid | 1.0 |
| Pyridoxal HCl | 20 |
| Pyridoxine HCl | 5.0 |
| Riboflavin | 20 |
| Thiamine HCl | 20 |
| Vitamin $B_{12}$ | 50 |
| Vitamin A | 10 |
| Citric Acid | 20 |
| Na—Acetate, 3 $H_2O$ | 100 |
| ATP (Na—salt) | 20 |
| Estradiol | 20 |
| Cholate | 25 |
| Deoxyadenosine | 15 |
| Deoxyguanosine | 15 |
| Dextrose | 1500 |
| Flavin Adenine Dinucleotide | 20 |
| Galactosamine | 120 |
| Glucose-1-phosphate | 25 |
| Glucuronolactone | 25 |
| Hypoxanthine | 100 |
| 5-Methyl-deoxycytidylic Acid | 5 |
| Phenol Red | 15 |
| Thioactic Acid | 2 |
| Thyroxine | 20 |
| UTP | 20 |
| PRPP | 50 |
| Acetyl Choline | 25 |
| Adenosine-5'-phosphate | 5 |
| Cholesterol | 5 |
| Coenzyme A | 50 |
| Deoxycytidine HCl | 15 |
| Deoxyribose | 50 |
| DPN | 10 |
| Fructose-1-6-diphosphate | 120 |
| Glucosamine | 50 |
| Glucuronate | 25 |
| Glutathione | 20 |
| Guanine | 50 |
| D-Ribose | 5 |
| Sodium pyruvate | 150 |
| Thymidine | 25 |
| TPN | 20 |
| Xanthine | 25 |
| Glycogen | 250 |
| Calcium Chloride | 150 |

TABLE 1-continued
COMPOSITION OF SERUM-FREE, SYNTHETIC, COMPLETELY CHEMICALLY DEFINED TISSUE CULTURE MEDIA - KUMAR MEDIA I

| Item | mg/liter |
| --- | --- |
| Potassium Chloride | 500 |
| Magnesium Sulfate | 250 |
| Ferric Ammonium Sulfate | 20 |
| $KH_2PO_4$ | 75 |
| Sodium Chloride | 6500 |
| Sodium Hydrogen Phosphate, disodium | 15 |
| Magnesium Chloride | 500 |
| L-Lecithin | 150 |
| Sphingomyelin | 75 |
| Gentamycin | 5 |

Sodium bicarbonate - up to 1500 mg/liter, sufficient to adjust final pH to 7.4
Mixture dissolved in Deionized, distilled water.

TABLE 2
COMPOSITION OF SERUM-FREE, SYNTHETIC, COMPLETELY CHEMICALLY DEFINED TISSUE CULTURE MEDIA - KUMAR MEDIA II

| Item | mg/liter |
| --- | --- |
| Alanine | 60 |
| Alpha-Amino-n-butyric Acid | 5 |
| Arginine | 150 |
| Asparagine | 5 |
| Aspartic Acid | 75 |
| Cysteine-HCl | 100 |
| Cystine | 25 |
| Ergothionine | 10 |
| Glutamic Acid | 500 |
| Glutamine | 800 |
| Glycine | 500 |
| Histidine, HCl | 50 |
| Homocysteine | 20 |
| Isoleucine | 75 |
| Leucine | 300 |
| Lysine HCl | 300 |
| Methionine | 50 |
| Ornithine, HCl | 10 |
| Phenylalanine | 100 |
| Proline | 100 |
| Serine | 75 |
| Taurine | 50 |
| Threonine | 100 |
| Tryptophane | 50 |
| Tyrosine | 100 |
| Valine | 200 |
| DL-Alpha-Tocopherol | 2.5 |
| Ascorbic Acid | 25 |
| Biotin | 20 |
| Calciferol | 2.5 |
| Ca—pentothenate | 25 |
| Choline Chloride | 25 |
| Cocarboxylase | 20 |
| Folic Acid | 20 |
| i-Inositol | 15 |
| Menadione | 2.5 |
| Niacin | 5.0 |
| Niacinamide | 20 |
| p-Amniobenzoic Acid | 1.0 |
| Pyridoxal HCl | 20 |
| Pyridoxine HCl | 5.0 |
| Riboflavin | 20 |
| Thiamine HCl | 20 |
| Vitamin $B_{12}$ | 50 |
| Vitamin A | 10 |
| Citric Acid | 20 |
| Na—Acetate, 3 $H_2O$ | 100 |
| ATP (Na—salt) | 20 |
| Estradiol | 20 |
| Cholate | 25 |
| Deoxyadenosine | 15 |
| Deoxyguanosine | 15 |
| Dextrose | 1500 |
| Flavin Adenine Dinucleotide | 20 |
| Galactosamine | 120 |
| Glucose-1-phosphate | 25 |
| Glucuronolactone | 25 |

TABLE 2-continued
COMPOSITION OF SERUM-FREE, SYNTHETIC, COMPLETELY CHEMICALLY DEFINED TISSUE CULTURE MEDIA - KUMAR MEDIA II

| Item | mg/liter |
| --- | --- |
| Hypoxanthine | 100 |
| 5-Methyl-deoxycytidylic Acid | 5 |
| Phenol Red | 15 |
| Thioactic Acid | 2 |
| Thyroxine | 20 |
| UTP | 20 |
| PRPP | 50 |
| Acetyl Choline | 25 |
| Adenosine-5'-phosphate | 5 |
| Cholesterol | 5 |
| Coenzyme A | 50 |
| Deoxycytidine HCl | 15 |
| Deoxyribose | 50 |
| DPN | 10 |
| Fructose-1-6-diphosphate | 120 |
| Glucosamine | 50 |
| Glucuronate | 25 |
| Glutathione | 20 |
| Guanine | 50 |
| D-Ribose | 5 |
| Sodium pyruvate | 150 |
| Thymidine | 25 |
| TPN | 20 |
| Xanthine | 25 |
| Glycogen | 250 |
| Calcium Chloride | 150 |
| Potassium Chloride | 500 |
| Magnesium Sulfate | 250 |
| Ferric Ammonium Sulfate | 20 |
| $KH_2PO_4$ | 75 |
| Sodium Chloride | 6500 |
| Sodium Hydrogen Phosphate, disodium | 15 |
| Magnesium Chloride | 500 |
| L-Lecithin | 150 |
| Sphingomyelin | 75 |
| Gentamycin | 5 |
| Colchicine | 0.0025 |
| Colcemid | 0.0025 |
| EDTA | 0.0050 |
| and Phytohegglutinin | 5 ml/liter |

Sodium bicarbonate - up to 1500 mg/liter sufficient to adjust final pH to 7.4
Mixture dissolved in Deionized, distilled water.

What is claimed is:

1. (a) A cell culturing medium comprising an amino acid composition containing:

| Item | mg/liter |
| --- | --- |
| Alanine | 60 |
| Alpha-Amino-n-butyric Acid | 5 |
| Arginine | 150 |
| Asparagine | 5 |
| Aspartic Acid | 75 |
| Cysteine-HCl | 100 |
| Cystine | 25 |
| Ergothionine | 10 |
| Glutamic Acid | 500 |
| Glutamine | 800 |
| Glycine | 500 |
| Histidine, HCl | 50 |
| Homocysteine | 20 |
| Isoleucine | 75 |
| Leucine | 300 |
| Lysine HCl | 300 |
| Methionine | 50 |
| Ornithine HCl | 10 |
| Phenylalanine | 100 |
| Proline | 100 |
| Serine | 75 |
| Taurine | 50 |
| Threonine | 100 |
| Tryptophane | 50 |
| Tyrosine | 100 |

-continued

| Item | mg/liter |
|---|---|
| and Valine | 200, |

(b) a vitamin mixture containing:

| Item | mg/liter |
|---|---|
| DL-Alpha-Tocopherol | 2.5 |
| Ascorbic Acid | 25 |
| Biotin | 20 |
| Calciferol | 2.5 |
| Calcium-pentothenate | 25 |
| Choline Chloride | 25 |
| Cocarboxylase | 20 |
| Folic Acid | 20 |
| i-Inositol | 15 |
| Menadione | 2.5 |
| Niacin | 5.0 |
| Niacinamide | 20 |
| p-Aminobenzoic Acid | 1.0 |
| Pyridoxal HCl | 20 |
| Pyridoxine HCl | 5.0 |
| Riboflavin | 20 |
| Thiamine HCl | 20 |
| Vitamin B12 | 50 |
| Vitamin A | 10 |
| and Citric Acid | 20, |

(c) other components containing:

| Item | mg/liter |
|---|---|
| Na—Acetate, 3 $H_2O$ | 100 |
| ATP (Sodium Salt) | 20 |
| Estradiol | 20 |
| Cholate | 25 |
| Deoxyadenosine | 15 |
| Deoxyguanosine | 15 |
| Dextrose | 1500 |
| Flavin Adenine Dinucleotide | 20 |
| Galactosamine | 120 |
| Glucose-1-phosphate | 25 |
| Glucuronolactone | 25 |
| Hypoxanthine | 100 |
| 5-Methyl-deoxycytidylic Acid | 5 |
| Phenol Red | 15 |
| Thioactic Acid | 2 |
| Thyroxine | 20 |
| UTP | 20 |
| PRPP | 50 |
| Acetylcholine | 25 |
| Adenosine-5'-phosphate | 5 |
| Cholesterol | 5 |
| Coenzyme A | 50 |
| Deoxycytidine HCl | 15 |
| Deoxyribose | 50 |
| DPN | 10 |
| Fructose-1-6-diphosphate | 120 |
| Glucosamine | 50 |
| Glucuronate | 25 |
| Glutathione | 20 |
| Guanine | 50 |
| D-Ribose | 5 |
| Sodium pyruvate | 150 |
| Thymidine | 25 |
| TPN | 20 |
| Xanthine | 25 |
| Glycogen | 250 |
| Calcium Chloride | 150 |
| Potassium Chloride | 500 |
| Magnesium Sulfate | 250 |
| Ferric Ammonium Sulfate | 20 |
| $KH_2PO_4$ | 75 |
| Sodium Chloride | 6500 |
| Sodium Hydrogen Phosphate, disodium | 15 |
| Magnesium Chloride | 500 |
| L-Lecithin | 150 |

-continued

| Item | mg/liter |
|---|---|
| and Sphingomyelin | 75, | and Sodium bicarbonate—upto 1500 mg/liter, sufficient to adjust final pH to 7.4.

2. A culture medium as defined in claim 1, in which the concentrations of the vitamin mixture identified in subsection (b) are in the following range:

| Item | mg/liter |
|---|---|
| DL-Alpha-Tocopherol | 2.0 to 3.0 |
| Ascorbic Acid | 20.0 to 30.0 |
| Biotin | 10.0 to 25.0 |
| Calciferol | 1.0 to 2.8 |
| Calcium-pentothenate | 15.0 to 25.0 |
| Choline Chloride | 15.0 to 25.0 |
| Cocarboxylase | 10.0 to 20.0 |
| Folic Acid | 10.0 to 20.0 |
| i-Inositol | 10.0 to 20.0 |
| Menadione | 2.0 to 3.0 |
| Niacin | 4.0 to 5.0 |
| Niacinamide | 4.0 to 20.0 |
| p-Aminobenzoic Acid | 0.1 to 1.0 |
| Pyridoxal HCl | 5.0 to 20.0 |
| Pyridoxine HCl | 2.0 to 5.0 |
| Riboflavin | 5.0 to 35.0 |
| Thiamine HCl | 5.0 to 35.0 |
| Vitamin B12 | 10.0 to 50.0 |
| Vitamin A | 5.0 to 20.0 |
| and Citric Acid | 10.0 to 20.0 |

3. A culture media, as defined in claim 2, further comprising:
Gentamycin: 5.0 mg/liter.

4. A culture media, as defined in claim 3, further comprising:

| Item | mg/liter |
|---|---|
| Colchicine | 0.0025 |
| Colcemid | 0.0025 |
| EDTA | 0.0050 |
| and Phytohemagglutinin | 5.0 ml/liter |

5. A culture media, as defined in claim 1, further comprising:
Gentamycin: 5.0 mg/liter.

6. A culture media, as defined in claim 3, further comprising:

| Item | mg/liter |
|---|---|
| Colchicine | 0.0025 |
| Colcemid | 0.0025 |
| EDTA | 0.0050 |
| and Phytohemagglutinin | 5.0 ml/liter |

7. An aqueous culture media, for use in cell growth comprising:

| Item | mg/liter |
|---|---|
| Alanine | 60 |
| Alpha-Amino-n-butyric Acid | 5 |
| Arginine | 150 |
| Asparagine | 5 |
| Aspartic Acid | 75 |
| Cysteine-HCl | 100 |
| Cystine | 25 |
| Ergothionine | 10 |

-continued

| Item | mg/liter |
|---|---|
| Glutamic Acid | 500 |
| Glutamine | 800 |
| Glycine | 500 |
| Histidine, HCl | 50 |
| Homocysteine | 20 |
| Isoleucine | 75 |
| Leucine | 300 |
| Lysine HCl | 300 |
| Methionine | 50 |
| Ornithine HCl | 10 |
| Phenylalanine | 100 |
| Proline | 100 |
| Serine | 75 |
| Taurine | 50 |
| Threonine | 100 |
| Tryptophane | 50 |
| Tyrosine | 100 |
| Valine | 200 |
| DL-Alpha-Tocopherol | 2.5 |
| Ascorbic Acid | 25 |
| Biotin | 20 |
| Calciferol | 2.5 |
| Calcium-pentothenate | 25 |
| Choline Chloride | 25 |
| Cocarboxylase | 20 |
| Folic Acid | 20 |
| i-Inositol | 15 |
| Menadione | 2.5 |
| Niacin | 5.0 |
| Niacinamide | 20 |
| p-Aminobenzoic Acid | 1.0 |
| Pyridoxal HCl | 20 |
| Pyridoxine HCl | 5.0 |
| Riboflavin | 20 |
| Thiamine HCl | 20 |
| Vitamin B12 | 50 |
| Vitamin A | 10 |
| Citric Acid | 20 |
| Na—Acetate, 3 H2O | 100 |
| ATP (Sodium salt) | 20 |
| Estradiol | 20 |
| Cholate | 25 |
| Deoxyadenosine | 15 |
| Deoxyguanosine | 15 |
| Dextrose | 1500 |
| Flavin Adenine Dinucleotide | 20 |
| Galactosamine | 120 |
| Glucose-1-phosphate | 25 |
| Glucuronolactone | 25 |
| Hypoxanthine | 100 |
| 5-Methyl-deoxycytidylic Acid | 5 |
| Phenol Red | 15 |
| Thioactic Acid | 2 |
| Thyroxine | 20 |
| UTP | 20 |
| PRPP | 50 |
| Acetylcholine | 25 |
| Adenosine-5'-phosphate | 5 |
| Cholesterol | 5 |
| Coenzyme A | 50 |
| Deoxycytidine HCl | 15 |
| Deoxyribose | 50 |
| DPN | 10 |
| Fructose-1-6-diphosphate | 120 |
| Glucosamine | 50 |
| Glucuronate | 25 |
| Glutathione | 20 |
| Guanine | 50 |
| D-Ribose | 5 |
| Sodium pyruvate | 150 |
| Thymidine | 25 |
| TPN | 20 |
| Xanthine | 25 |
| Glycogen | 250 |
| Calcium Chloride | 150 |
| Potassium Chloride | 500 |
| Magnesium Sulfate | 250 |
| Ferric Ammonium Sulfate | 20 |
| KH2PO4 | 75 |
| Sodium Chloride | 6500 |
| Sodium Hydrogen Phosphate, disodium | 15 |
| Magnesium Chloride | 500 |
| L-Lecithin | 150 |
| Sphingomyelin | 75 |

Sodium bicarbonate - up to 1500 mg/liter, sufficient to adjust final pH to 7.4 and Sodium bicarbonate—upto 1500 mg/liter, sufficient to adjust final pH to 7.4.

8. An aqueous culture media as defined in claim 7, wherein the vitamin concentrations are as follows:

| Item | mg/liter |
|---|---|
| DL-Alpha-Tocopherol | 2.0 to 3.0 |
| Ascorbic Acid | 20.0 to 30.0 |
| Biotin | 10.0 to 25.0 |
| Calciferol | 1.0 to 2.8 |
| Calcium-pentothenate | 15.0 to 25.0 |
| Choline Chloride | 15.0 to 25.0 |
| Cocarboxylase | 10.0 to 20.0 |
| Folic Acid | 10.0 to 20.0 |
| i-Inositol | 10.0 to 20.0 |
| Menadione | 2.0 to 3.0 |
| Niacin | 4.0 to 5.0 |
| Niacinamide | 4.0 to 20.0 |
| p-Aminobenzoic Acid | 0.1 to 1.0 |
| Pyridoxal HCl | 5.0 to 20.0 |
| Pyridoxine HCl | 2.0 to 5.0 |
| Riboflavin | 5.0 to 35.0 |
| Thamie HCl | 5.0 to 35.0 |
| Vitamin B12 | 10.0 to 50.0 |
| Vitamin A | 5.0 to 20.0 |
| and Citric Acid | 10.0 to 20.0. |

9. A culture media, as defined in any one of the claims 1 thru 8, wherein said medium is free of cell-damaging qualities of proteolytic enzymes.

10. A method for growing human amniotic fluid cells comprising culturing human amniotic fluid cells in the culture media as defined in any one of claims 1 to 8.

11. A method for growing human or animal neural tissues comprising culturing human or animal neural cells in the culture media defined in anyone of claims 1 to 8.

* * * * *